United States Patent

Martret et al.

[11] 3,966,950
[45] June 29, 1976

[54] NOVEL THERAPEUTIC COMPOSITIONS AND METHOD INVOLVING THIAZOL-CARBOXAMIDES

[75] Inventors: Odile Le Martret, Paris; Francois Clemence, Rosny-sous-Bois, both of France

[73] Assignee: Roussel-UCLAF, Paris, France

[22] Filed: Jan. 8, 1975

[21] Appl. No.: 539,327

Related U.S. Application Data

[62] Division of Ser. No. 340,289, March 12, 1973, Pat. No. 3,872,124.

[30] Foreign Application Priority Data

Mar. 22, 1972    France .............................. 72.10010

[52] U.S. Cl. .................................. 424/250
[51] Int. Cl.² ................................... A61K 31/495
[58] Field of Search ............................. 424/250

[56] References Cited
UNITED STATES PATENTS

| | | |
|---|---|---|
| 3,530,131 | 9/1970 | de Stevens .......................... 424/250 |
| 3,658,822 | 4/1972 | Fauran et al ......................... 424/250 |

*Primary Examiner*—Sam Rosen
*Attorney, Agent, or Firm*—Hammond & Littell

[57] ABSTRACT

Novel thiazolcarboxamides of the formula

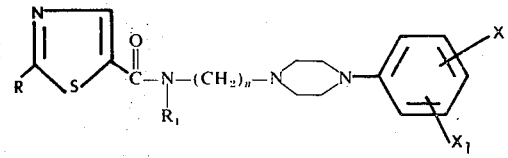

wherein R is selected from the group consisting of alkyl of 1 to 6 carbon atoms and phenyl, $R_1$ is selected from the group consisting of hydrogen and alkyl of 1 to 4 carbon atoms, $n$ is a whole number from 2 to 5 and X and $X_1$ are individually selected from the group consisting of hydrogen, halogen, trifluoromethyl and alkyl, alkoxy and alkylthio of 1 to 4 carbon atoms and their non-toxic, pharmaceutically acceptable acid addition salts having α-adrenolytic activity and their preparation.

9 Claims, No Drawings

NOVEL THERAPEUTIC COMPOSITIONS AND METHOD INVOLVING THIAZOL-CARBOXAMIDES

PRIOR APPLICATION

This application is a division of our copending, commonly assigned U.S. patent application Ser. No. 340,289 filed Mar. 12, 1973, now U.S. Pat. No. 3,872,124.

STATE OF THE ART

Belgium Pat. No. 736,219 describes various thiazol-5-carboxylic acids having vasodilatatory and hypolipemiant activity. French BSM Pat. No. 7590 teaches aryl piperazinyl alkylene carboxamides of thiophenes which possess anti-depressive, analgesic anti-inflammatory and diuretic activity.

OBJECTS OF THE INVENTION

It is an object of the invention to provide the novel thiazol-5-caboxamides of formula I.

It is another object of the invention to provide a novel process for the preparation of the compounds of formula I.

It is a further object of the invention to provide novel α-adrenolytic compositions and to provide a novel method of treating hypertension in warm-blooded animals.

These and other objects and advantages of the invention will become obvious from the following detailed description.

THE INVENTION

The novel products of the invention are selected from the group consisting of thiazolcarboxamides of the formula

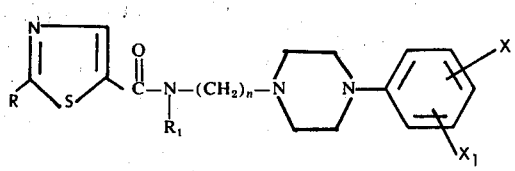

wherein R is selected from the group consisting of alkyl of 1 to 6 carbon atoms and phenyl, $R_1$ is selected from the group consisting of hydrogen and alkyl of 1 to 4 carbon atoms, n is a whole number from 2 to 5 and X and $X_1$ are individually selected from the group consisting of hydrogen, halogen, trifluoromethyl and alkyl, alkoxy and alkylthio of 1 to 4 carbon atoms and their non-toxic, pharmaceutically acceptable acid addition salts.

Among the preferred substituents are R as alkyl such as methyl, ethyl, n-propyl, n-butyl or n-pentyl, $R_1$, X and $X_1$ as alkyl such as methyl or ethyl and X and $X_1$ as halogens such as fluorine, bromine or chlorine or alkoxy or alkylthio such as methoxy, ethoxy, ethylthio or methylthio. The preferred compounds of formula I are those where X is o-methoxy, $X_1$ is hydrogen, R is ethyl, propyl or phenyl and $R_1$ is hydrogen or methyl and n is 2 or 4.

The non-toxic, pharmaceutically acceptable acid addition salts may be derived from an inorganic acid such as hydrochloric acid, hydrobromic acid, sulfuric acid or phosphoric acid and organic acids such as acetic acid, benzoic acid, tartaric acid, fumaric acid, maleic acid, methane sulfonic acid or p-toluenesulfonic acid.

The process of the invention for the preparation of the compounds of formula I comprises reacting a thiazol-5-carboxylic acid of the formula

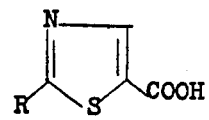

wherein R is alkyl of 1 to 6 carbon atoms or phenyl or a functional derivative thereof with a phenylpiperazine of the formula

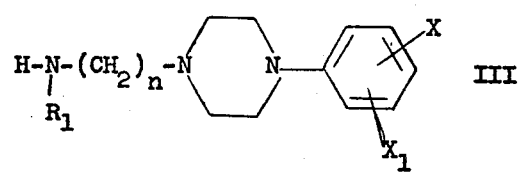

wherein $R_1$, X, $X_1$ and n have the above definitions to form the desired thaizol-5-carboxamide of formula I which may be treated with an acid to form the corresponding acid addition salt.

The functional derivatives of the thiazol-5-carboxylic acids of formula II may be the anhydride, the acid chloride, lower alkyl ester or mixed acid anhydride which have been classically used to form amides.

When using the free acid of formula II, the reaction is preferably effected by heating with the amine of formula III in the presence of a dehydrating agent such as dicyclohexylcarbodiimide. When using a lower alkyl ester of the acid of formula II, the reaction may be effected by simply heating with the amine of formula III.

When using the acid chloride or anhydride, the reaction is effected in an inert organic solvent such as aromatic hydrocarbons like toluene, xylene or benzene or ethyl ether or chloroform. If a mixed anhydride is used, it preferably is a mixed carbonic acid anhydride of the formula

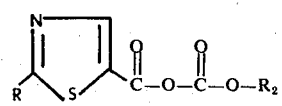

wherein R has the above definition and $R_2$ is alkyl of 1 to 6 carbon atoms and is preferably prepared by reacting an alkyl chloroformate of the formula $Cl-COOR_2$ with a salt, i.e. triethylamine, of the acid of formula II. The reaction with the amine of formula III is preferably effected with a solvent such as acetone.

The amines of formula III used as starting materials are known or easily prepared by known processes. For example, when $R_1$ is hydrogen, a halonitrile of the formula

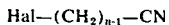

wherein Hal is a halogen and $n$ is 2 to 5 is reacted with a phenylpiperazine of the formula

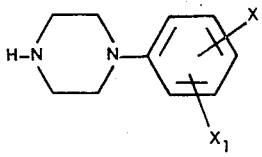

to form a compound of the formula

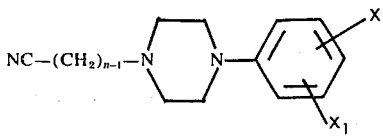

and the nitrile may be reduced as taught by Mull et al [J. Med. Pharm. Chem., Vol. 5 (1962), p. 944–949]. Where $R_1$ is alkyl, the amines may be prepared as described in Example 4.

The novel α-adrenolytic compositions of the invention are comprised of an effective amount of a compound of formula I or a non-toxic, pharmaceutically acceptable acid addition salt thereof and a pharmaceutical carrier. The compositions may be in the form of tablets, sublingual tablets, dragees, capsules, gelules, drinkable solutes or suspensions or suppositories or in the form of injectable solution or suspensions.

The compositions have an α-adrenolytic activity and are distinguished from the free acids from which the carboxamides of formula I are derived by not presenting any notable peripheric vasodilatatory activity while manifesting a sedative activity.

The novel method of the invention for treating hypertension in warm-blooded animals comprises administering to warm-blooded animals a hypotensively effective amount of a compound of formula I or a non-toxic, pharmaceutically acceptable acid addition salt thereof. The products may be administered orally, perlingerally, parenterally or rectally. The usual daily dose is 0.2 to 10 mg/kg depending upon the product and the method of administration.

In the following examples there are described several preferred embodiments to illustrate the invention. However, it should be understood that the invention is not intended to be limited to the specific embodiments.

EXAMPLE 1

N-β-[4'-(o-methoxyphenyl)-1'-piperazinyl]-ethyl-2-n-propylthiazol-5-carboxamide

A solution of 8.7 g of ethyl chloroformate in 30 ml of acetone was added with stirring and cooling to 6° to 8°C to a suspension of 11.1 g of 2-n-propyl-5-carboxythiazol in 80 ml of acetone to which a solution of 7.2 g of triethylamine in 30 ml of acetone had been added. After returning the mixture to room temperature, the mixture was stirred for 30 minutes and then was filtered to remove the triethylamine hydrochloride formed. The filtrate was cooled to 8°C and a solution of 11.4 g of 4-(o-methoxyphenyl)-1-(β-aminoethyl)-piperazine in 30 ml of acetone was added thereto. The mixture stood for 48 hours and then the acetone was evaporated. The oil residue was taken up in 300 ml of ethyl ether and 20 ml of water and the ether phase was washed with a 20% aqueous potassium carbonate solution until the wash water were neutral and then with water, dried over magnesium sulfate and evaporated to dryness. The residue was crystallized from isopropyl ether to obtain 8.4 g of N-β-[4'-(o-methoxyphenyl)-1'-piperazinyl]-ethyl-2-n-propylthiazol-5-carboxamide in the form of colorless crystals melting at 113°C.

Analysis: $C_{20}H_{28}N_4O_2S$; molecular weight = 388.53; Calculated: %C, 14.42; %S, 8.23. Found: %C, 14.32; %S, 8.16.

5 ml of an ethanolic hydrochloric acid solution titrating 4.29 N were added to a solution of 8.4 g of N-β-[4'-(o-methoxyphenyl)-1'-piperazinyl]-ethyl-2-n-propylthiazol-5-carboxamide in 43 ml of ethanol and the mixture was filtered. The recovered precipitate was crystallized from ethanol to obtain 7.4 g of N-β-[4'-(o-methoxyphenyl)-1'-piperazinyl]-ethyl-2-n-propylthiazol-5-carboxamide hydrochloric melting at 180°C. The product occurred as colorless crystals soluble in water, methanol and ethanol and insoluble in benzene and ethyl ether.

Analysis: $C_{20}H_{28}N_4O_2S \cdot HCl$; molecular weight = 424.98; Calculated: %C, 56.52; %H, 6.88; %Cl, 8.34; %N, 13.18; %S, 7.55. Found: %C, 56.3; %H, 6.7; %Cl, 8.4; %N, 13.1; %S, 7.4.

EXAMPLE 2

N-β-[4'-(o-methoxyphenyl)-1'-piperazinyl]-ethyl-2-ethylthiazol-5-carboxamide

A solution of 3.2 g of triethylamine in 10 ml of acetone was added to a suspension of 4.5 g of 2-ethyl-5-carboxythiazole in 30 ml of acetone and after cooling the mixture of 6°C, a solution of 3.3 g of ethyl chloroformate in 15 ml of acetone was added with stirring while keeping the temperature at 6° to 8°C. After raising the temperature to room temperature, the mixture was stirred for 30 minutes and then filtered to remove the precipitate formed. The filtrate was cooled to 8°C and a solution of 5.9 g of 4-(o-methoxyphenyl)-1-(β-aminoethyl)-piperazine in 15 ml of acetone was added thereto. The mixture stood for 16 hours and the acetone was then evaporated. The oily residue was taken up in 100 ml of methylene chloride and 10 ml of water and the organic phase was washed with aqueous 10% potassium carbonate solution until the wash waters were neutral, then with water, dried over magnesium sulfate and evaporated to dryness. The residue was taken up in 20 ml of isopropyl ether and the solution was filtered. The precipitate was crystallized from cyclohexane to obtain 4.4 g of N-β-[4'-(o-methoxyphenyl)-1'-piperazinyl]-ethyl-2-ethylthiazol-5-carboxamide melting at 110°C. The product occurred in the form of colorless crystals soluble in methanol, ethanol, acetone and chloroform and insoluble in water.

Analysis: $C_{19}H_{26}N_4O_2S$; molecular weight = 374.49; Calculated: %C, 60.93; %H, 7.00; %N, 14.96; %S, 8.56. Found: %C, 61.1; %H, 6.9; %N, 14.6; %S, 8.2.

3.05 ml of an ethanolic hydrochloric acid solution titrating 3.15 N were added to a solution of 3.6 g of N-β-[4'-(o-methoxyphenyl)-1'-piperazinyl]-ethyl-2-ethylthiazol-5-carboxamide in 20 ml of ethanol and the mixture was filtered. The recovered precipitate was crystallized from ethanol to obtain 2.95 g of N-β-[4'-(o-methoxyphenyl)-1'-piperazinyl]-ethyl-2-ethylthiazol-5-carboxamide hydrochloride melting at 190°C. The product occurred as colorless crystals soluble in water, methanol, ethanol and chloroform.

Analysis: $C_{19}H_{26}N_4O_2S \cdot HCl$; molecular weight = 410.96; Calculated: %C, 55.53; %H, 6.62; %Cl, 8.63; %N, 13.63; %S, 7.80. Found: %C, 55.6; %H, 6.7; %Cl, 8.6; %N, 13.4; %S, 7.7.

EXAMPLE 3

N-β-[4'-(o-methoxyphenyl)-1'-piperazinyl]-ethyl-2-phenylthiazol-5-carboxamide

A solution of 3.65 g of triethylamine in 15 ml of acetone was added to a suspension of 6.8 g of 2-phenyl-5-carboxythiazole [prepared by process of J.A.C.S., Vol. 65 (1943), p. 2167] in 35 ml of acetone and after cooling to 3°C, a solution of 3.8 g of ethyl chloroformate in 20 ml of acetone was added thereto. The solution stood for 30 minutes at room temperature and the precipitate formed was filtered off. The filtrate was cooled to 6°C and then a solution of 6.8 g of 4-(o-methoxyphenyl)-1-(β-aminoethyl)-piperazine in 35 ml of acetone was added thereto while maintaining the temperature at 6° to 9°C. The mixture was then allowed to stand overnight at room temperature and was filtered. The precipitate recovered was washed with acetone to obtain 4 g of colorless crystals melting at 152°C. The filtrate was evaporated to dryness and the residue was dissolved in 100 ml of methylene chloride. The organic solution was washed with water, then with aqueous 10% potassium carbonate solution and finally with water, dried over magnesium sulfate and evaporated to dryness under reduced pressure. The residue was crystallized from ether, recovered by filtration and crystallized from ethanol to obtain 3 g of raw product melting at 151°–152°C. The combined products were crystallized from ethanol to obtain 6.2 g of N-β-[4'-(o-methoxyphenyl)-1'-piperazinyl]-ethyl-2-phenylthiazol-5-carboxamide melting at 152°C. The product occurred as colorless crystals soluble in chloroform, slightly soluble in ethanol and N hydrochloric acid and in soluble in water and ether.

Analysis: $C_{23}H_{26}N_4O_2S$; molecular weight = 422.54; Calculated: %C, 65.37; %H, 6.20; %N, 13.26; %S, 7.59. Found: %C, 65.3; %H, 6.1; %N, 13.2; %S, 7.8.

4.8 ml of ethanolic 3.15 N hydrochloric acid were added to a solution of 5.9 g of the above 2-phenyl-thaizol-5-carboxamide in 750 ml of ethyl acetate and the mixture was filtered. The recovered precipitate was washed with ethyl acetate and was crystallized from ethanol containing 5% water to obtain 3.45 g of N-β-[4'-(o-methoxyphenyl)-1'-piperazinyl]-ethyl-2-phenyl-thiazol-5-carboxamide hydrochloride melting at 244°C. The product occurred in the form of colorless crystals soluble in chloroform, slightly soluble in water and insoluble in ether and acetone.

Analysis: $C_{23}H_{27}ClN_4O_2S$; molecular weight = 459; Calculated: %C, 60.18; %H, 5.93; %Cl, 7.72; %N, 12.21; %S, 6.98. Found: %C, 60.2; %H, 5.7; %Cl, 7.9; %N, 12.1; %S, 6.8.

EXAMPLE 4

N-methyl-N-β-[4'-(o-methoxyphenyl)-1'-piperazinyl]-ethyl-2-n-propylthiazol-5-carboxamide

STEP A:

4-(o-methoxyphenyl)-1-chloroethyl-piperazine . HCl 79.4 ml of ethanolic 3.15 N hydrochloric acid were added to a solution of 29.5 g of 4-(o-methoxyphenyl)-1-hydroxyethyl-piperazine (described in U.S. Pat. No. 2,836,595) in 1000 ml of ethyl ether and the mixture was filtered. The precipitate recovered was washed with ethyl ether to obtain 38 g of 4-(o-methoxyphenyl)-1-hydroxyethyl-piperazine.HCl. The said product was suspended in 370 ml of 1,1-dioxide of tetrahydrothiophene and after adding 13.3 ml of thionyl chloride to the solution, the mixture was heated at 120°C for 20 minutes. After cooling, the solution was poured into 2 liters of benzene and the mixture was filtered. The precipitate recovered was crystallized from ethanol to obtain 20.2 g of 4-(o-methoxyphenyl)-1-chloroethyl-piperazine hydrochloride melting at 195°C. The free base was obtained by treating the hydrochloride with potassium carbonate and it melted at 36°C.

STEP B:

4-(o-methoxyphenyl)-1-(β-methylaminoethyl)-piperazine 8 ml of ethanol were added to a mixture of 8.9 g of 4-(o-methoxyphenyl)-1-chloroethyl-piperazine .HCl in 20 g of an aqueous solution of 34.88% methylamine and the mixture was stirred for 1 hour at room temperature and then for 4 hours at reflux. The ethanol was evaporated and after cooling the mixture, 5 g of sodium hydroxide pellets were added thereto. The mixture was extracted with ethyl ether and the extracts were dried over potassium carbonate and the solvent was evaporated. The oily residue was distilled to obtain 2.6 g of 4-(o-methoxyphenyl)-1-(β-methylaminoethyl)-piperazine in the form of a yellow oil boiling at 153°C under 0.2 mm Hg. The oil was soluble in ethanol and ethyl ether and slightly soluble in water.

Analysis: $C_{14}H_{23}N_3O$; molecular weight = 249.36; Calculated: %N, 16.85. Found: %N, 16.5.

STEP C:

N-methyl-N-β-[4'-(o-methoxyphenyl)-1'-piperazinyl]-ethyl-2-n-propylthiazol-5-carboxamide A solution of 1.01 g of triethylamine in 5 ml of acetone was added to a suspension of 1.60 g of 2-n-propyl-5-carboxythiazole in 10 ml of acetone and after cooling to 4°C, a solution of 1.04 g of ethyl chloroformate in 5 ml of acetone was added thereto. The precipitate formed was removed by filtration and after cooling the filtrate, a solution of 1.83 g of 4-(o-methoxyphenyl)-1-(β-methylaminoethyl)-piperazine in 5 ml of acetone was added thereto. The mixture stood overnight and the acetone was then evaporated. The residue was taken up in 30 ml of methylene chloride and 5 ml of water and the organic phase was washed with an aqueous 10% potassium carbonate solution, then with water, dried over magnesium sulfate and evaporated to dryness. The residue was chromatographed over silica gel and eluted with a 6-4 acetone-cyclohexane mixture to obtain 1.04 g of N-methyl-N-β-[4'-(o-methoxyphenyl)-1'-piperazinyl]-ethyl-2-n-propylthiazol-5-carboxamide in the form of colorless crystals melting at 65°C.

The latter product and 0.50 g of the said product produced in another preparation were dissolved in 7 ml of ethanol and 1.3 ml of an ethanolic 3.15 N hydrochloric acid solution were added thereto. The precipitate formed was recovered by filtration and was crystallized from isopropanol to obtain 1.25 g of N-methyl-N-β-[4'-(o-methoxyphenyl)-1'-piperazinyl]-ethyl-2-n-propylthiazol-5-carboxamide hydrochloride melting at 185°C. The product occurred as colorless crystals soluble in chloroform and water, slightly soluble in ethanol and insoluble in ether.

Analysis: $C_{21}H_{31}ClN_4O_2S$; molecular weight = 439.02; Calculated: %C, 57.45; %H, 7.12; %N, 12.76; %Cl, 8.07; %S, 7.30. Found: %C, 57.1; %H, 7.1; %N, 12.6; %Cl, 8.1; %S, 7.5.

EXAMPLE 5

N-δ-[4'-(o-methoxyphenyl)-1'-piperazinyl]-butyl-2-n-propylthiazol-5-carboxamide 5.1 g of triethylamine were added to a solution of 8.6 g of 2-n-propyl-5-carboxythiazole in 50 ml of toluene and then a solution of 5.5 g of ethyl chloroformate in 20ml of toluene was added thereto at −20°C. Then, a solution of 15 g of 4-(o-methoxyphenyl)-1-(δ-aminobutyl)-piperazine (described in U.S. Pat. No. 3,398,151) in 50 ml of toluene was added and the mixture was stirred for 15 hours at room temperature. The solution was washed with water, dried and concentrated to dryness and the residue was crystallized from an isopropyl ether-isopropanol mixture to obtain 7.5 g of N-δ-[4'-(o-methoxphenyl)-1'-piperazinyl]-butyl-2-n-propylthiazol-5-carboxamide melting at 100°C.

Analysis: $C_{22}H_{32}N_4O_2S$; molecular weight = 416.6; Calculated: %C, 63.43; %H, 7.74; %N, 13.45; %S, 7.70. Found: %C, 63.4; %H, 7.9; %N, 13.7; %S, 7.6.

EXAMPLE 6

N-β-[4'-(o-methoxyphenyl)-1'-piperazinyl]-ethyl-2-n-propylthiazole-5-carboxamide

STEP A: Thiobutyramide

A mixture of 71 g of butyronitrile and 35 g of diethylamine was heated to 50°–60°C and the solution was saturated by bubbling hydrogen sulfide therethrough. After the addition in 500 ml of water, the mixture was extracted with ethyl ether and the ether phase was washed with aqueous 10% hydrochloric acid solution and then with water until the wash waters were neutral. The ether phase was dried over magnesium sulfate and the ethyl ether was removed by distillation to obtain 87 g of thiobutyramide which was used as is for the next step.

STEP B: Ethyl 2-n-propylthiazol-5-carboxylate

A mixture of 38 g of thiobutyramide, 54.2 g of ethyl 2-formyl-2-chloro-acetate, 185 ml of dioxane and 22 g of magnesium carbonate was heated for 4 hours at 60°C and the precipitate formed was removed by filtration. The dioxane was distilled from the filtrate and the residue was taken up in 665 ml of a 1-1 ethyl ether-water mixture. The ether phase was recovered by decantation and was washed with aqueous 10% hydrochloric acid solution and then with water until the wash waters were neutral, dried over magnesium sulfate and distilled to dryness. The residue was distilled to obtain 57 g of ethyl 2-n-propylthiazol-5-carboxylate boiling at 95°–106°C under 0.5 mm Hg.

STEP C:

N-β-[4'-(o-methoxyphenyl)-1'-piperazinyl]-ethyl-2-n-propylthiazol-5-carboxamide 7 g of 4-(o-methoxyphenyl)-1-(β-aminoethyl)-piperazine were melted at 40°C and 6 g of ethyl 2-n-propylthiazol-5-carboxylate were added thereto. The mixture was heated for 3 ½ hours at 125°C under a nitrogen atomsphere and after returning to room temperature, 20 ml of ethyl ether were added thereto. The mixture was ground and allowed to stand overnight. The precipitate was recovered by filtration and was washed with ethyl ether and crystallized from isopropyl ether to obtain 5.5 g of N-β-[4'-(o-methoxyphenyl)-1'-piperazinyl]-ethyl-2-n-propylthiazol-5-carboxamide identical to the product of Example 1.

EXAMPLE 7

An injectable solution was prepared by dissolving 10 mg (calculated as free base) of N-β-[4'-(o-methoxyphenyl)-1'-piperazinyl]-ethyl-2-ethylthiazol-5-carboxamide hydrochloride with sufficient aqueous excipient to obtain a final solution of 3 ml.

EXAMPLE 8

Tablets were prepared by through admixing of 50 ma of N-β-[4'-(o-methoxyphenyl)-1'-piperazinyl]-ethyl-2-ethylthiazol-5-carboxamide hydrochloride and 500 mg of an excipient consisting of lactose, amidon, talc and magnesium stearate.

PHARMACOLOGICAL DATA

A. In Vitro Adrenolytic Activity

A withdrawn portion of the duodenum of a rabbit was placed in a bath containing oxygenated tyrode liquid at 37°C and the sensibility of the duodenum to a dose of 0.01 γ/ml for 30 seconds of adrenaline was determined. The test product was contacted with the organ for 30 seconds and immediately afterwards, the organ was subjected to adrenaline at a dose of 0.01 γ/ml for 30 seconds. The dose of the test compound which inhibited 50% of decontractions due to adrenaline ($DA_{50}$) was determined. The test products used in solution in physiological serum and the muscle contractions were recorded on a myograph. The results are shown in Table I.

TABLE I

| Product | $DA_{50}$ in γ/ml |
| --- | --- |
| N-β-[4'-(o-methoxyphenyl)-1'-piperazinyl]-ethyl-2-n-propyl-thiazol-5-carboxamide hydrochloride (compound A) | 0.5 |
| N-β[4'-(o-methoxyphenyl)-1'-piperazinyl]-ethyl-2-ethyl-thiazol-5-carboxamide hydrochloride (compound B) | 0.1 to 0.5 |
| N-methyl-N-β-[4'-(o-methoxyphenyl)-1'-piperazinyl]ethyl-2-n-propylthiazol-5-carboxamide hydrochloride (compound C) | 0.1 to 0.5 |

The results of Table I show that the products possess an important "in vitro" adrenolytic activity at a dose of 0.1 to 0.5 γ/ml.

B. In Vivo adrenolytic activity

The normal carotidien pressure on rats was recorded and the modifications of adrenalinic hypertensive activity as influenced by an injection of the test product were observed. The adrenalin and the test product were injected into the juglar vein and the dose of product needed to reduce by 50% the hypertensive action of adrenaline ($DA_{50}$) was determined. The results are reported in Table II.

TABLE II

| Products | $DA_{50}$ in mg/kg |
| --- | --- |
| A | 0.1 to 0.25 |
| B | 0.1 |
| C | 0.5 |
| N-β-[4'-(o-methoxyphenyl)-1'-piperazinyl]-ethyl-2-phenyl-thiazol-5-carboxamide hydrochloride (compound D) | 0.5 to 1 (intraperitoneal) |
| N-δ-[4'-(o-methoxyphenyl)-1'-piperazinyl]-butyl-2-n-propyl-thiazol-5-carboxamide (compound E) | 0.1 |

The results of Table II show that the test products have an important "in vivo" adrenolytic activity at a dose of 0.1 to 1.0 mg/kg.

C. Hypotensive activity

The test products were administered intravenously (juglar vein) to groups of rats and the level of the carotid blood pressure was recorded. The $DA_{30}$ dose, dose which reduced by 30% of carotidien pressure, was determined 30 minutes after administration of the product. The results are reported in Table III.

TABLE III

| Product | $DA_{30}$ in mg/kg at 30 mm |
| --- | --- |
| A | 0.25 to 0.5 |
| B | 0.5 |
| C | 0.5 |
| D | 0.5 to 1 (intraperitoneal) |

The results of Table III show that the test products have an important hypotensive activity at a dose of 0.1 to 1 mg/kg.

D. Acute Toxicity

The acute toxicity was determined on groups of mice weighing 18 to 22 g and the test products were administered intravenously or intraperitoneally in increasing doses as a suspension in water containing gum. The results were held under observation for a week and the $DL_{50}$ dose was determined graphically by the method of Dragstedt and Lang. The results are reported in Table IV.

TABLE IV

| Product | $DL_{50}$ in mg/kg Intravenous | Intraperitoneal |
| --- | --- | --- |
| A | 35 | 82 |
| B | 57 | 124 |
| C | 43 | 110 |
| D | insoluble | 325 |
| E | — | 80 |

Various modifications of the products and compositions of the invention may be made without departing from the spirit or scope thereof and it is to be understood that the invention is to be limited only as defined in the appended claims.

We claim:

1. An α-adrenolytic composition comprising an effective amount of a compound selected from the group consisting of thiazolcarboxamides of the formula

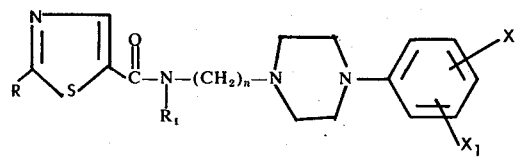

wherein R is selected from the group consisting of alkyl of 1 to 6 carbon atoms and phenyl, $R_1$ is selected from the group consisting of hydrogen and alkyl of 1 to 4 carbon atoms, n is a whole number from 2 to 5 and X and $X_1$ are individually selected from the group consisting of hydrogen, halogen, trifluoromethyl and alkyl, alkoxy and alkylthio of 1 to 4 carbon atoms and their non-toxic, pharmaceutically acceptable acid addition salts and a pharmaceutical carrier.

2. A method of treating hypertension in warm-blooded animals comprising administering a hypotensively effective amount of a compound selected from the group consisting of thaizolcarboxamides of the formula

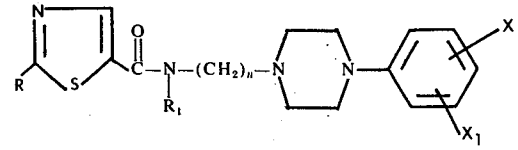

wherein R is selected from the group consisting of alkyl of 1 to 6 carbon atoms and phenyl, $R_1$ is selected from the group consisting of hydrogen and alkyl of 1 to 4 carbon atoms, n is a whole number from 2 to 5 and X and $X_1$ are individually selected from the group consisting of hydrogen, halogen, trifluoromethyl and alkyl, alkoxy and alkylthio of 1 to 4 carbon atoms and their non-toxic, pharmaceutically acceptable acid addition salts.

3. The method of claim 2 wherein $X_1$ is hydrogen and X is o-methoxy.

4. The method of claim 3 wherein R is selected from the group consisting of ethyl, propyl and phenyl and $R_1$ is selected from the group consisting of hydrogen and methyl and n is 2 or 4.

5. The method of claim 2 wherein the compound is selected from the group consisting of N-β-[4'-(o-methoxyphenyl)-1'-piperazinyl]-ethyl-2-n-propyl-thiazol-5-carboxamide and its non-toxic, pharmaceutically acceptable acid addition salts.

6. The method of claim 2 wherein the compound is selected from the group consisting of N-β-[4'-(o-methoxyphenyl)-1'-piperazinyl]-ethyl-2-ethylthiazole-5-carboxamide and its non-toxic, pharmaceutically acceptable acid addition salts.

7. The method of claim 2 wherein the compound is selected from the group consisting of N-β-[4'-(o-methoxyphenyl)-1'-piperazinyl]-ethyl-2-phenyl-thiazole-5-carboxamide and its non-toxic, pharmaceutically acceptable acid addition salts.

8. The method of claim 2 wherein the compound is selected from the group consisting of N-methyl-N-β-[4'-(o-methoxyphenyl)-1'-piperazinyl]-ethyl-2-n-propylthiazol-5-carboxamide and its non-toxic, pharmaceutically acceptable acid addition salts.

9. The method of claim 2 wherein the compound is selected from the group consisting of N-δ-[4'-(o-methoxyphenyl)-1'-piperazinyl]-butyl-2-n-propyl-thiazol-5-carboxamide and its non-toxic, pharmaceutically acceptable acid addition salts.

* * * * *